US006982562B2

(12) United States Patent
Rains et al.

(10) Patent No.: US 6,982,562 B2
(45) Date of Patent: Jan. 3, 2006

(54) MULTIPLE FREQUENCY GRAIN MOISTURE SENSOR FOR COMBINES

(75) Inventors: Gerald E. Rains, Bettendorf, IA (US); James J. Phelan, Bettendorf, IA (US); Zachary W. Slavens, Bettendorf, IA (US); Andrzej Kozicki, Milan, IL (US); Robert C. Funk, Auburn, IL (US)

(73) Assignee: Deere & Company, Moline, IL (US)

( * ) Notice: Subject to any disclaimer, the term of this patent is extended or adjusted under 35 U.S.C. 154(b) by 11 days.

(21) Appl. No.: 11/145,755

(22) Filed: Jun. 6, 2005

(65) Prior Publication Data

US 2005/0225334 A1    Oct. 13, 2005

Related U.S. Application Data

(62) Division of application No. 10/718,147, filed on Nov. 20, 2003, now Pat. No. 6,917,206, which is a division of application No. 10/145,463, filed on May 14, 2002, now Pat. No. 6,647,653, and a division of application No. 10/003,884, filed on Oct. 25, 2001, now Pat. No. 6,686,749.

(51) Int. Cl.
*G01R 27/26* (2006.01)
(52) U.S. Cl. .................................... 324/694; 324/664
(58) Field of Classification Search ............... 324/664, 324/667, 670, 689, 640, 643; 73/73, 861.73; 73/ 318/483
See application file for complete search history.

(56) References Cited

U.S. PATENT DOCUMENTS

| 2,665,409 | A | 1/1954 | Rogers |
| 2,788,487 | A | 4/1957 | Grogg, Jr. |
| 3,482,162 | A | 12/1969 | Wochowski |
| 3,760,267 | A | 9/1973 | Williams |
| 3,826,979 | A | 7/1974 | Steinmann |
| 3,870,951 | A | 3/1975 | Brown et al. |
| 4,547,725 | A | 10/1985 | Oetiker et al. |
| 4,584,655 | A | 4/1986 | Funk et al. |
| 4,599,809 | A | 7/1986 | Parkes |
| 4,853,614 | A | 8/1989 | Carver |
| 4,896,795 | A | 1/1990 | Ediger et al. |

(Continued)

FOREIGN PATENT DOCUMENTS

CA    2 182 989    8/1996

(Continued)

OTHER PUBLICATIONS

Combine Dealer's Dream, Shivers, Corydon, IA, no month or year available.

(Continued)

*Primary Examiner*—Vincent Q. Nguyen

(57) ABSTRACT

A grain moisture sensing system having an excitation signal source for producing an excitation signal. A sensor cell having a driven plate and a sense plate that applies to the excitation signal for captive measurement between the driven plate and the sense plate to produce a current at the sense plate. Connected to the excitation source is a first synchronous detector and connected to the sense plate is a second synchronous detector.

5 Claims, 8 Drawing Sheets

U.S. PATENT DOCUMENTS

| | | | |
|---|---|---|---|
| 4,956,591 A * | 9/1990 | Schierbeek et al. | 318/483 |
| 5,092,819 A | 3/1992 | Schroeder et al. | |
| 5,218,309 A | 6/1993 | Nelson et al. | |
| 5,343,761 A | 9/1994 | Myers | |
| 5,561,250 A | 10/1996 | Myers | |
| 5,957,773 A | 9/1999 | Olmsted et al. | |
| 6,121,782 A | 9/2000 | Adams et al. | |
| 6,155,103 A | 12/2000 | Diekhans et al. | |
| 6,285,198 B1 | 9/2001 | Nelson et al. | |
| 6,388,453 B1 | 5/2002 | Greer | |

FOREIGN PATENT DOCUMENTS

| | | |
|---|---|---|
| EP | 0 389 320 | 9/1990 |
| EP | 1072 885 A2 | 6/2000 |
| GB | 2 087 704 A | 6/1982 |

OTHER PUBLICATIONS

Combine Calc-U-Dri Monitor Grain Moisture Continuously as you Harvest, DMC, no month or year available.

* cited by examiner

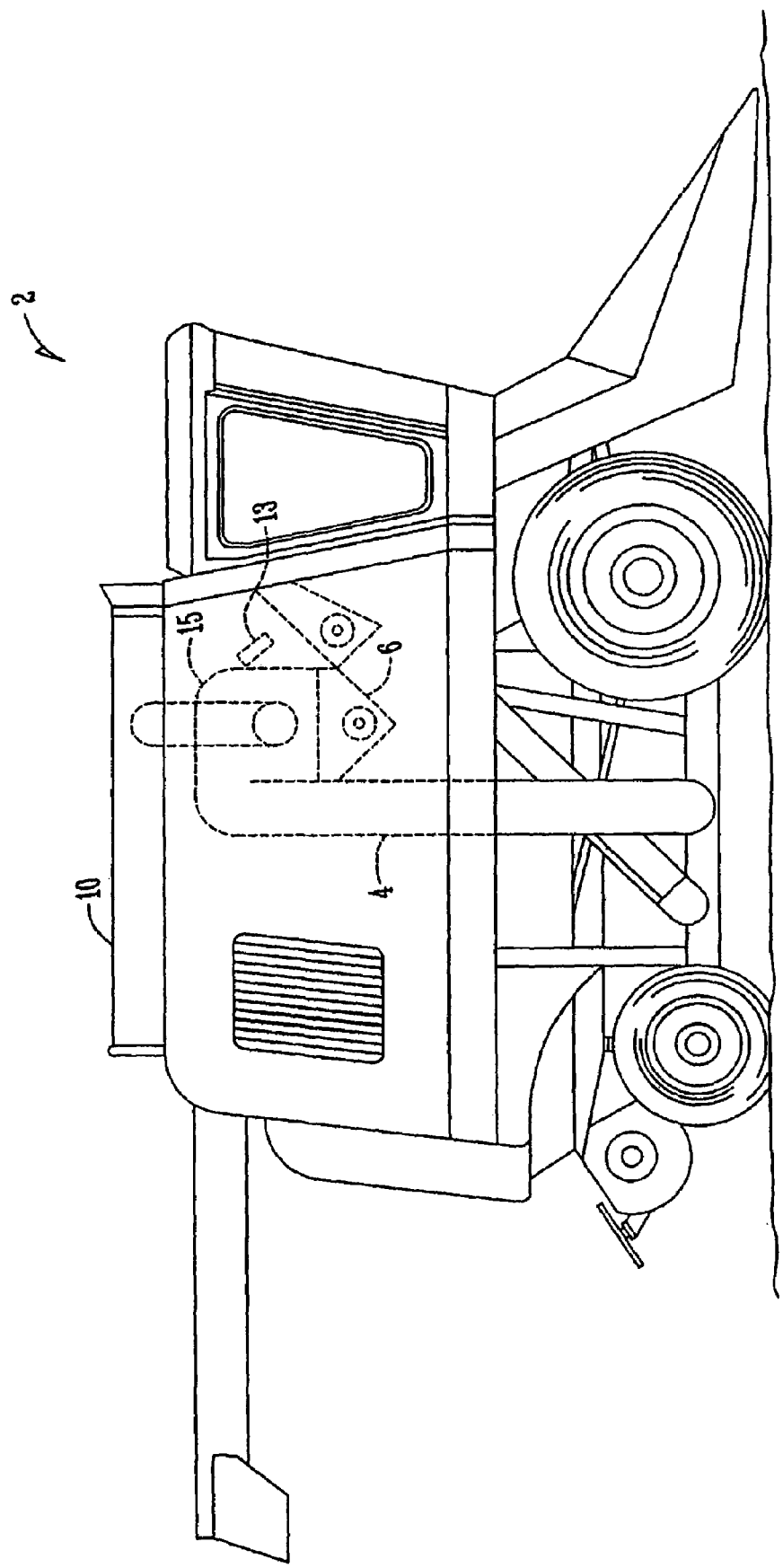

US 6,982,562 B2

MULTIPLE FREQUENCY GRAIN MOISTURE SENSOR FOR COMBINES

CROSS REFERENCE TO A RELATED APPLICATION

This application is a division of U.S. application Ser. 10/718,147 filed Nov. 20, 2003 now U.S. Pat. No. 6,917,206, which is a division of Ser. No. 10/145,463 filed May 14, 2002, now U.S. Pat. No. 6,647,653 and is a division of 10/003,884 file Oct. 25, 2001, now U.S. Pat. No. 6,686,749 issued Feb. 3, 2004.

BACKGROUND OF THE INVENTION

1) Field of the Invention

The present invention relates generally to grain moisture sensors. More specifically, the present invention relates to an improved grain moisture sensor for combines.

2) Related Art

Grain moisture sensors have been used in combines, particularly in precision agriculture applications. Continuous or instantaneous grain moisture readings allow an operator to observe the moisture of the grain as it is being harvested. In conjunction with a GPS unit, a moisture sensor can be used to provide moisture mapping. In addition, moisture sensors are used in yield monitoring applications. When used in combination with a grain flow sensor, the moisture sensor information is often used to calculate the number of dry bushels in a field and the number of bushels per acre based on the number of wet bushels and the moisture content.

Moisture sensors in combines are commonly mounted in one of two places. The first of these places is in the grain tank auger. The grain tank auger is also known as the loading auger in a combine. There are a number of problems with mounting the moisture sensor in this location. The first is that in order to mount the moisture sensor the flighting of the loading auger must be removed. With removed flighting, material can build up which requires the operator to clean the sensor. If the moisture sensor is not kept clean, readings may be inaccurate or the moisture sensor may be inoperable.

A further problem with mounting the moisture sensor in the loading auger of a combine is the lag time or delay encountered when measuring moisture. When the moisture sensor is mounted in the loading auger position, moisture sensor readings are not taken until the grain is actually in the loading auger of the combine. Therefore, grain must travel up the elevator and fill the sump of the transition housing before the auger is able to deliver grain to the sensor and a moisture measurement can be taken. This deficiency frustrates the use of a moisture sensor in precision agriculture applications, making it more difficult to correctly associate a particular field location with a particular grain moisture.

A further problem with mounting grain moisture sensors in a loading auger is that such a moisture system does not provide for determining when there is sufficient grain present for a grain moisture measurement. Grain moisture sensors usually include capacitive plates. The volume between the plates must be covered before an accurate grain moisture measurement can be made. A moisture sensor that is not filled with grain is not accurately measuring the moisture of the grain. Therefore, this inability to know when the capacitive plate is covered can result in erroneous grain moisture measurements.

Another location that has been used to mount grain moisture sensors is on the side of the clean grain elevator. The clean grain elevator mounting location is thought to provide a steadier flow of grain. Further, the clean grain elevator location may avoid causing accelerated wear of the auger assembly and does not obstruct grain flow in the manner which the loading auger location may. Despite these improvements, a number of problems remain with mounting a moisture sensor on the side of the clean grain elevator in a combine. One problem relates to the slow cycle time of the moisture sensor. In a low flow condition which is not uncommon in grain harvesting, the sensor can be extremely slow to fill. For example, it may take up to four minutes to fill the sensor. Therefore, the number of moisture sensor readings is reduced and the moisture sensor data is insufficient for providing accurate measurements for moisture maps, yield determinations, and other purposes.

A further problem with mounting moisture sensors on the side of the clean grain elevator relates to the sensitivity of this mounting location in the presence of side slopes. It is not uncommon for a combine to be operating on a hill or slope. When the combine is operated on a slope such that the grain flow is directed away from the moisture sensor inlet, it is nearly impossible to fill the grain moisture sensor with sufficient grain to make a moisture determination.

A further problem with mounting moisture sensors on the clean grain elevator relates to grain leaks. When mounted on the side of the clean grain elevator, any grain leaks that occur result in the leaking grain spilling on the ground, as the grain leaks are not contained.

Another problem in grain moisture sensing relates to the sensor cell. Typically, the sensor cell consists of a parallel plate capacitor in which the grain serves as the dielectric material. The cell capacitance and therefore the permittivity of the grain between the plates is measured. From this measurement, the moisture of the grain is determined. Normally, these cell designs are not as close to an ideal parallel plate capacitor as desired. In particular, prior art designs for grain moisture sensors for use in combines use cells that are subject to electric field fringe effects. A fringe effect occurs when electric field lines are not both straight and perpendicular to the plates of the parallel plate capacitor. These fringe effects produce an uncontrollable influence on the measurements from material other than grain that is close to the cell but outside of the cell. Another problem with cell designs is that they do not produce uniformly dense electric field lines between the parallel plates. The nonuniform electric field density creates the problem of unequal sensitivity to grain throughout the cell. Thus the measurements of the moisture of the grain within the cell are not as accurate as desired in these respects.

Another problem relating to the prior art relates to the method for measuring cell capacitance. Measuring the capacitance of a cell filled with grain is a traditional way of obtaining grain moisture. There are two common prior art methods for measuring cell capacitance. The first method is to sense the changes in frequency of a variable oscillator that uses cell capacitance as one of its frequency determining elements. The second method is to excite the cell capacitance with a signal having a known frequency and to measure the absolute value of the resulting cell current, usually with a bridge type of circuit and a peak detector, and then to calculate the capacitance of the cell. Both of these methods tend to be dependent on grain cell construction and are sensitive to noise, changes in circuit characteristics, and parasitic effects. The first method also has the problem of poor control of frequency, especially as moisture varies. Both of these methods are also single dimensional, lacking the ability to measure both the dielectric and the loss properties of the grain. Therefore numerous problems remain with this type of sensing.

The combination of the dielectric and loss parameters is known as the complex permittivity. Complex permittivity is an intrinsic, frequency dependent material property. The knowledge of the grain's complex permittivity at more than one frequency has been found to be a part of advanced moisture level assessment as has been demonstrated by USDA studies. Despite this observation, problems remain.

BRIEF SUMMARY OF THE INVENTION

It is therefore an object of the present invention to provide a grain moisture sensor for use on a combine that improves upon the state of the art.

It is another object of the present invention to provide a grain moisture sensor that provides accurate and consistent grain moisture measurements.

It is a further object of the present invention to provide a grain moisture sensor that does not require the removal of flighting in the loading auger for cleaning.

Yet another object of the present invention is to provide a grain moisture sensor that avoids lags in time between when grain is harvested and when the moisture measurement is taken.

A further object of the present invention is to provide a grain moisture sensor that is capable of determining when the sensor cell is full.

Yet another object of the present invention is to provide an improved grain moisture sensor that is less affected by low flow conditions.

Yet another object of the present invention is to provide a grain moisture sensor for use in a combine that is insensitive to changes in the side slope of the ground being harvested.

Yet another object of the present invention is to provide a grain moisture sensor that contains grain leaks.

A still further object of the present invention is to provide a grain moisture sensor with a cell that has characteristics closer to an ideal parallel plate capacitor.

A still further object of the present invention is to provide a grain moisture sensor that provides for uniform electric field density to allow for equal sensitivity to grain throughout the cell.

Yet another object of the present invention is to provide a grain moisture sensor with a cell for reducing fringe effects produced by material other than grain that may be close to, but outside of the cell.

Yet another object of the present invention is to provide a grain moisture sensor that provides for increased protection from electromagnetic interference.

A still further object of the present invention is to provide a grain moisture sensor that provides for the measurement of complex permittivity of the grain.

Another object of the present invention is to provide a grain moisture sensor that provides for the measurement of complex permittivity of the grain at more than one frequency.

A grain moisture sensor of the present invention provides for the sensing of the moisture of grain being harvested by a combine. One aspect of the present invention relates to the location of the grain moisture sensor on the combine. According to the present invention, the grain moisture sensor is mounted off of the front of the clean grain elevator transition housing inside of the grain tank. This provides the advantages of access to the grain moisture sensor if required and the advantage that all leaks are contained. A further advantage is that the grain moisture sensor fills positively with grain. Further, this location of the grain moisture sensor allows for the sensor to always be filled regardless of the slope conditions of the combine.

Another aspect of the present invention relates to the cell design of the sensor. The cell of the present invention includes a driven plate to which excitation voltages are applied, a sense plate proximate and parallel to the driven plate for measuring current that passes through the cell, a fill plate adjacent to the sense plate for determining when the cell is full, and a guard adjacent to the sense plate and the fill plate for protecting the sense plate and the fill plate. The guard is electrically isolated from, but at the same potential as a sensed plate. The guard is parallel to and dimensionally larger than the sense plate in order to shape the electric field. The presence of the guard plate provides the advantage of straight electric field lines perpendicular to the sense plate and of uniform density throughout the region between the parallel plates. This results in reduced fringe effects and uniform electric field density allowing for equal sensitivity to grain throughout the cell. In addition, the guard shields the sense plate from external electric fields generated by sources other than the driven plate. The fill plate provides the advantage of accurate determination of whether or not the cell is full.

A further aspect of the present invention is the method in which the capacitance of a cell filled with grain is measured. The present invention provides for measurement of the complex permittivity of the grain. Further, the present invention provides for measurement of the complex permittivity at more than one frequency. This provides the advantage of permitting compensation for variations in grain density and conductivity effects which is particularly important in mobile moisture sensing applications such as the use of a moisture sensor on a combine. According to this aspect of the present invention, the circuit measures the real and imaginary components of both the excitation voltage and the sense current. From these values, the complex admittance of the cell is calculated. The measurements are repeated for the empty cell and the cell filled with grain. When the empty cell is not available, the calibrated reference admittances are used instead. The grain complex permittivity can then be calculated from these measurements. Mixers are used in the measurement of real and imaginary components of the voltage and current. This synchronous detection method has a very narrow band filtering effect, greatly reducing noise influence on the measurement. A virtual ground method of measuring low-level currents is used to provide the advantage of a substantial reduction in the influence of parasitic elements at the current sensing node. In addition, measurements can be corrected with the calibrated references to compensate for any environmental changes that may influence the circuit characteristics. This provides the advantage of securing stable and repetitive results.

In this matter, the present invention provides advantages in an improved grain moisture sensor.

BRIEF DESCRIPTION OF THE DRAWINGS

FIG. 1A is a side view that shows a combine with a grain moisture sensor according to the present invention.

DETAILED DESCRIPTION OF THE INVENTION

Figure 1B:
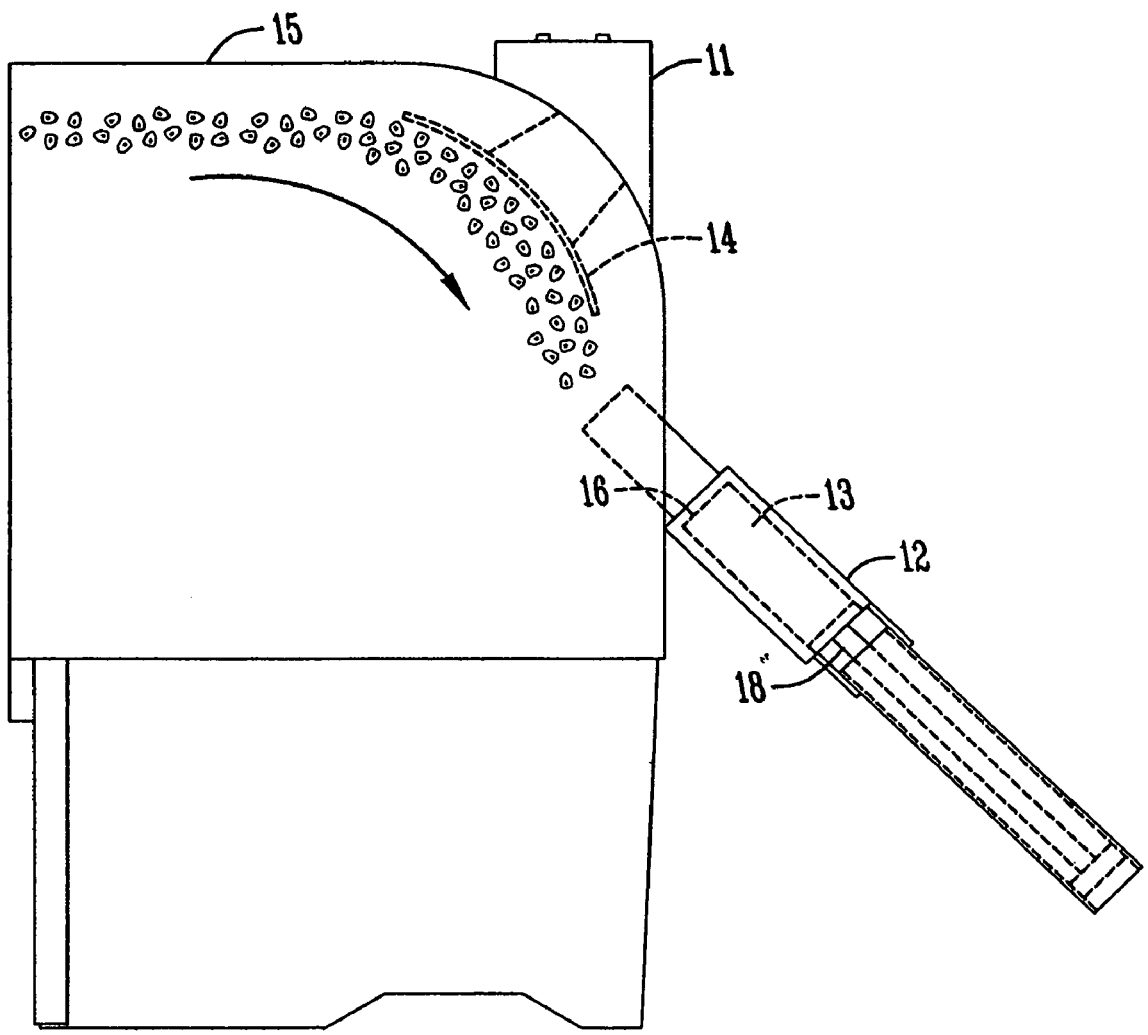
FIG. 1B is a side view of the grain moisture sensor of the present invention mounted in a combine and in a fill position.

FIG. 1A shows a combine having a grain moisture sensor according to the present invention. In FIG. 1A, the combine 2 is shown with a grain tank 10. In addition, the clean grain elevator 4 is shown. Grain from the clean grain elevator 4 travels to the transition housing 15 of the grain tank 10. The sump 6 of the transition housing is also shown.

Figure 1C:
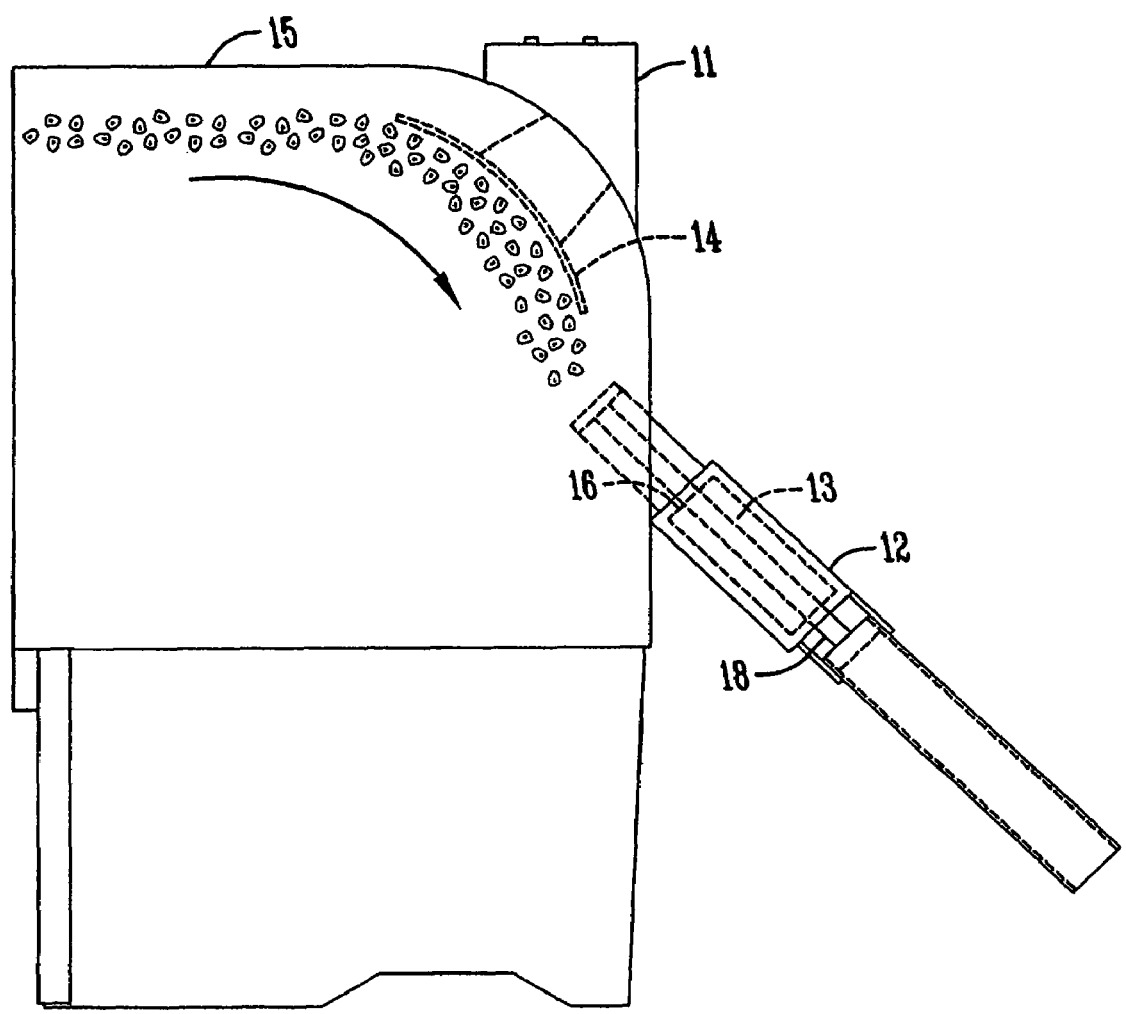
FIG. 1C is a side view of the grain moisture sensor of the present invention mounted in a combine in a sensing position.

FIGS. 1B and 1C show side views of the grain moisture sensor of the present invention as mounted in a combine. The grain tank 10 shown includes the grain moisture sensor 12. The grain moisture sensor 12 is located in the grain tank 10 of the combine near the mass flow sensor 11. The cell opening 16 is located below the impact plate 14 in the transition housing 15. Although an impact plate 14 is shown, the present invention contemplates that other deflectors can be used. In this location, the cell 13 is positively filled due to the direct or indirect velocities of grain created from the clean grain elevator paddles (not shown). This permits the cell 13 to be filled at high rates. This reduces any problems with slow cycle times associated with low flow conditions as here, the cell 13 is filled at a high rate due to its placement within the stream of grain created by the clean grain elevator. The cell 13 is placed in line with the cell inlet. A plunger/piston 18 with an electric actuator is used to force the grain sample back out of the inlet opening. In FIG. 1C, the cell 13 and plunger/piston 18 are in a sensing position.

Figure 2:
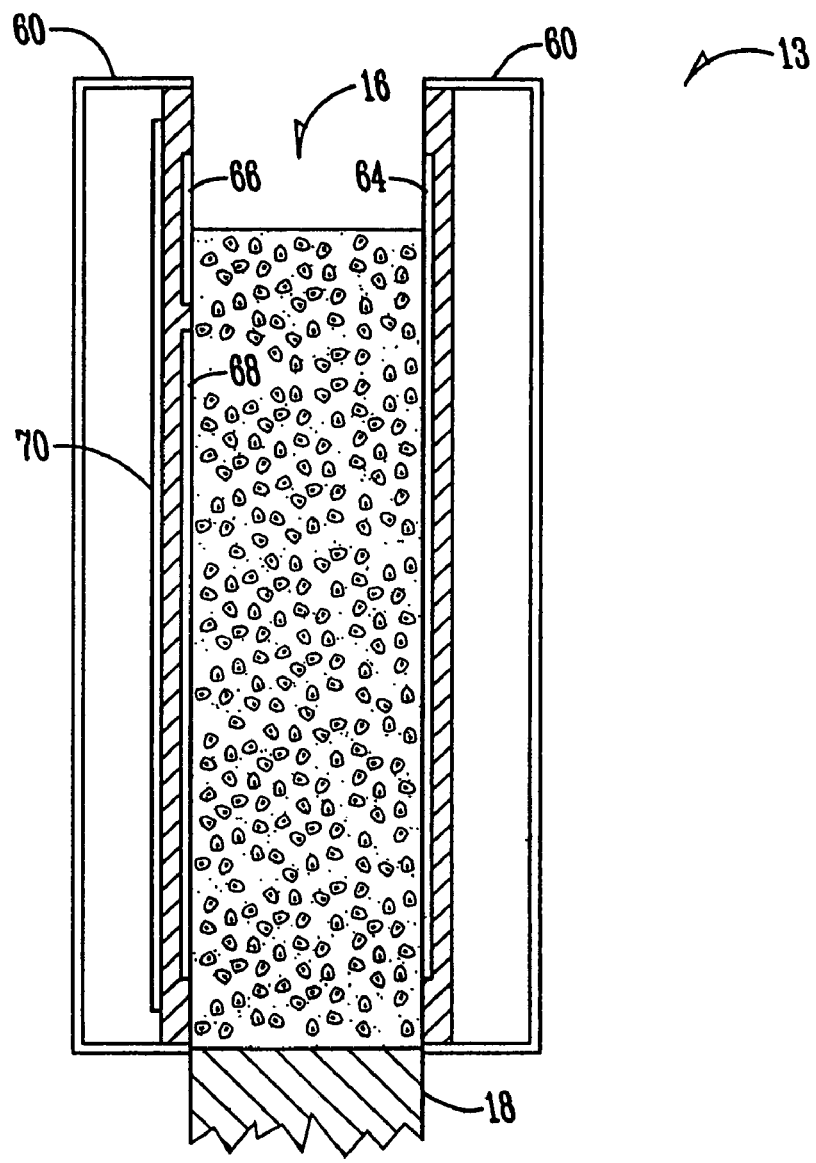
FIG. 2 is a side cross section of the cell of the grain moisture sensor of the present invention.

FIG. 2 illustrates a side view of the cell 13 of the present invention. The cell opening 16 or spacing is filled with grain. On either side of the spacing are parallel capacitor plates 64 and 68. The driven plate 64 is the plate to which an excitation voltage is applied. The sense plate 68 is the plate at which current is measured passing through the cell. The fill plate 66 is adjacent to the sense plate 68 and parallel to the driven plate 64.

The fill sensor plate is one-fourth the size of the sense plate. To determine when the cell is full, the fill plate should indicate a measured reading of one-fourth the sense plate measured reading. Although in this embodiment the fill sensor is one-fourth the size of the sense plate, the present invention contemplates numerous variations in the sizes of the plates. This is merely one example of a relative size which is convenient and useful.

The guard 70 is strategically placed behind the sense plate 68 and the fill plate 66. The guard 70 is parallel to and dimensionally larger than the sense plate 68 in order to shape the electric field. In addition, the guard 70 also shields the sense plate from external electric fields generated by sources other than the driven plate 64.

Figure 3:
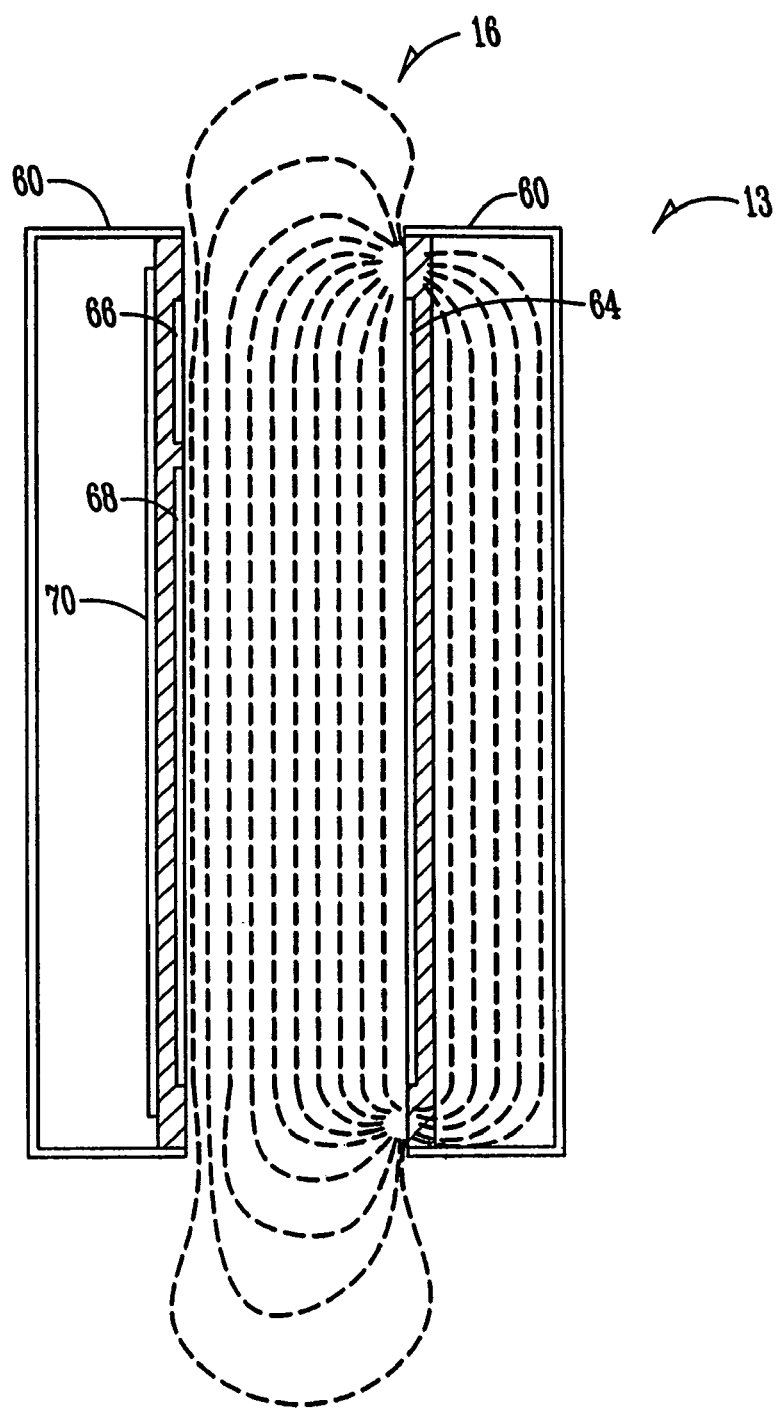
FIG. 3 is a side cross section of the cell of FIG. 2 showing the equipotential lines of the electric field that is created when an excitation voltage is applied to the driven plate of the present invention.

FIG. 3 illustrates the cell of the moisture sensor with the equipotential lines of the electric field that is generated when an excitation signal is applied to the driven plate 64. Due to the placement of the shield or guard 70, which is electrically isolated from but at the same potential as the sense plate 68, the effect on the electric field lines in the vicinity of the sense plate is to produce the equivalent of an ideal parallel plate capacitor without fringe effects. The electric field lines are straight in nature and perpendicular to the sense and fill plates. Further, the electric field lines are uniform in density throughout the region between the parallel plates. The result is that fringe effects are reduced. Fringe effects produce uncontrollable influence on the measurements from material other than the grain that are close to but outside of the cell. Here, the straight electric field lines within the cell show that the cell is largely immune from that influence. Further, the uniform electric field density provides for equal sensitivity to grain throughout the entire cell. In addition, the entire cell and the electronics are contained in a metal enclosure 60. The metal enclosure 60 serves as an electromagnetic interference shield, further isolating the entire cell from other sources of electromagnetic energy.

Figure 4:
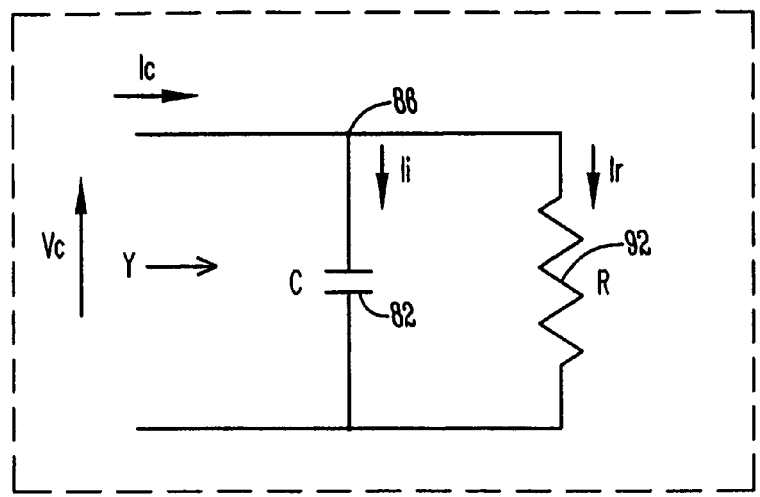
FIG. 4 is a circuit schematic of a model for the capacitor cell according to the present invention.

The present invention provides for grain moisture calculations based on the measurement of the complex relative permittivity of the grain (henceforth referred to as "complex permittivity"). FIG. 4 illustrates a schematic diagram of a circuit that is electrically equivalent to the capacitor cell of the present invention. This equivalent circuit includes an ideal capacitor 82 having a value of C in parallel with an ideal resistor 92 having a value of R. The ideal capacitor 82 represents the capacitive or energy storing property of the cell and the ideal resistor 92 represents the conductive or energy dissipating property of the cell. C and R are dependent on the frequency of excitation and on the moisture, temperature, and certain other properties of the grain.

The complex admittance of the cell is $$Y = \frac{1}{R} + j \cdot \omega \cdot C$$

where
$\omega = 2 \cdot \pi \cdot F$
f=frequency of excitation
j=the imaginary unit When the cell is empty it has essentially no energy dissipating properties. Its admittance is very close to that of an ideal capacitor having a value of $C_{CE}$:

$$Y_{CE} = j \cdot \omega \cdot C_{CE}$$

When the cell is filled with grain it has both energy dissipating and energy storing properties. Its admittance is $$Y_{CF} = \frac{1}{R_{CF}} + j \cdot \omega \cdot C_{CF}$$

Dividing the filled cell admittance by the empty cell admittance gives $$\frac{Y_{CF}}{Y_{CE}} = \frac{\frac{1}{R_{CF}} + j \cdot \omega \cdot C_{CF}}{j \cdot \omega \cdot C_{CE}} = \frac{\frac{1}{R_{CF}}}{j \cdot \omega \cdot C_{CE}} + \frac{C_{CF}}{C_{CE}}$$

$$= \frac{C_{CF}}{C_{CE}} - j \cdot \frac{1}{\omega \cdot C_{CE} \cdot R_{CE}} = \varepsilon$$

This ratio is the complex permittivity of the grain. Complex permittivity is an intrinsic material property, dependent only on the frequency of excitation and on the moisture, temperature, and certain other properties of the grain. It is independent of the dimensions and shape of the cell. Complex permittivity is commonly written as follows:

$$\epsilon = \epsilon' - j\epsilon''$$

where
  $\epsilon'$=dielectric constant
  $\epsilon''$=loss factor

It is an objective of the circuitry of the present invention to measure the empty cell admittance and the full cell admittance in order to use the above equations to compute the complex permittivity of the grain. As shown on FIG. 4, the complex excitation voltage, $V_C$, is applied across the circuit. The resulting complex current, $I_C$, flows through the circuit. $V_C$ has real component $V_r$ and imaginary component $V_i$:

$$V_C = V_r + j \cdot V_i$$

Ic has real component $I_r$ and imaginary component $I_i$:

$$I_C = I_r + j \cdot I_i$$

By measuring $V_r$, $V_i$, $I_r$, and $I_i$, the complex admittance Y can be calculated using complex arithmetic:

$$Y = \frac{I_C}{V_C} = \frac{I_r + j \cdot I_i}{V_r + j \cdot V_i}$$

Figure 5:
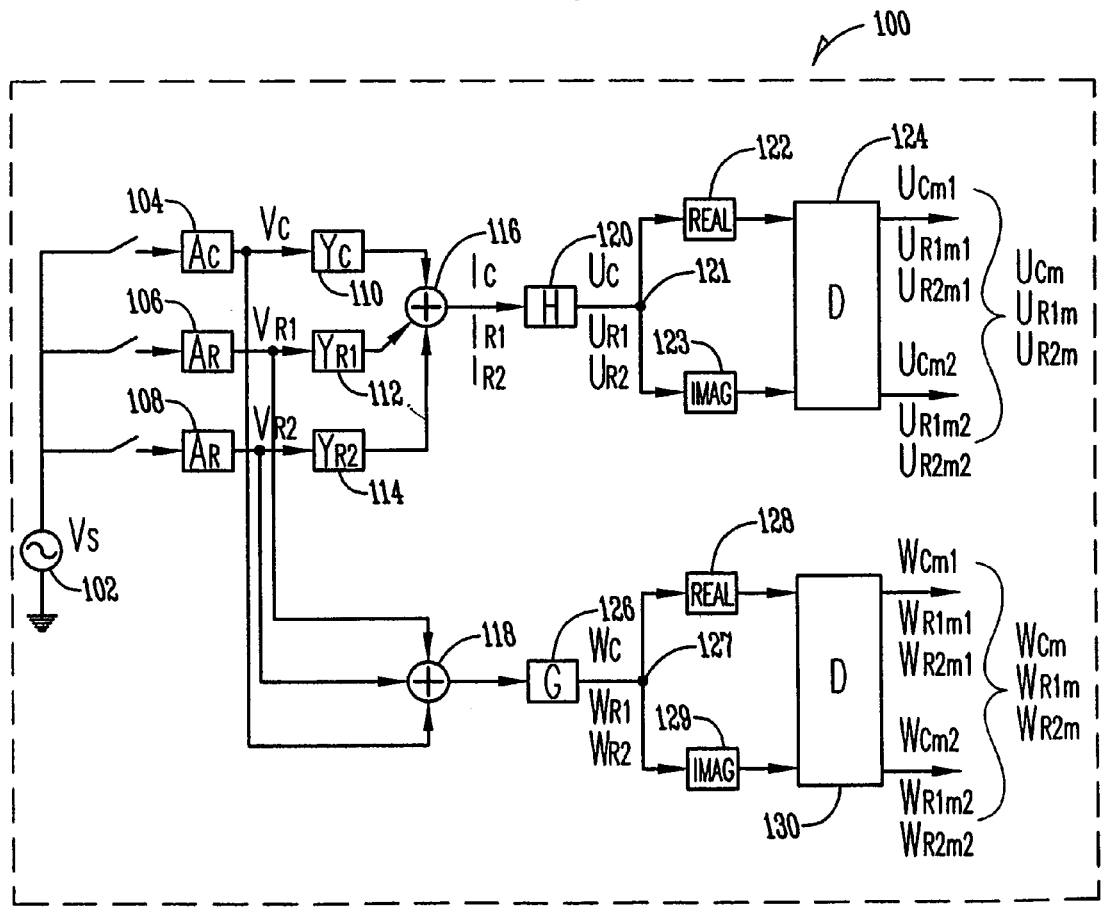
FIG. 5 is a block diagram of the admittance measuring circuit according to the grain moisture sensor of the present invention.

FIG. 5 illustrates the admittance measuring circuit used in the grain moisture sensor according to the present invention. In FIG. 5, the admittance measuring circuit 100 is shown. For explanation purposes, the following definitions are used:
$U_{R1m}$ is defined as the measured value of $U_{R1}$ defined below.
$U_{R1m1}$ is the real part (in phase signal value) of $U_{R1m}$
$U_{R1m2}$ is the imaginary part (quadrature signal value) of $U_{R1m}$.
$U_{R2m}$ is defined as the measured value of $U_{R2}$ defined below.
$U_{R2m2}$ is the real part (in phase signal value) of $U_{R2m}$
$U_{R2m2}$ is the imaginary part (quadrature signal value) of $U_{R2m}$.
$U_{Cm}$ is defined as the measured value of $U_C$ defined below.
$U_{Cm1}$ is the real part (in phase signal value) of $U_{Cm}$
$U_{Cm2}$ is the imaginary part (quadrature signal value) of $U_{Cm}$.
$W_{R1m}$ is defined as the measured value of $W_{R1}$ defined below.
$W_{R1m1}$ is the real part (in phase signal value) of $W_{R1m}$
$W_{R1m2}$ is the imaginary part (quadrature signal value) of $W_{R1m}$.
$W_{R2m}$ is defined as the measured value of $W_{R2}$ defined below.
$W_{R2m2}$ is the real part (in phase signal value) of $W_{R2m}$
$W_{R2m2}$ is the imaginary part (quadrature signal value) of $W_{R2m}$.
$W_{Cm}$ is defined as the measured value of $W_C$ defined below.
$W_{Cm1}$ is the real part (in phase signal value) of $W_{Cm}$
$W_{Cm2}$ is the imaginary part (quadrature signal value) of $W_{Cm}$.
$U_C$ is defined as a complex voltage value that represents the current passing through the cell.
$U_{R1}$ is defined as a complex voltage value that represents the current passing through the first reference.
$U_{R2}$ is defined as a complex voltage value that represents the current passing through the second reference.
$W_C$ is defined as a complex voltage value that represents the voltage across the cell.
$W_{R1}$ is defined as a complex voltage value that represents the voltage across the first reference.
$W_{R2}$ is defined as a complex voltage value that represents the voltage across the second reference.
$I_C$ is the complex current passing through the cell.
$I_{R1}$ is the complex current passing through the first reference.
$I_{R2}$ is the complex current passing throughout the second reference.
$V_C$ is the complex voltage across the cell.
$V_{R1}$ is the complex voltage across the first reference.
$V_{R2}$ is the complex voltage across the second reference.
$Y_C$ is the complex admittance of the cell.
$Y_{R1}$ is the complex admittance of the first reference.
$Y_{R2}$ is the complex admittance of the second reference.
H is the transfer function of the circuitry that performs complex current measurements.
G is the transfer function of the circuitry that performs complex voltage measurements.
$V_S$ is the generated source voltage.
$A_C$ is the transfer function for cell drive voltage.
$A_R$ is the transfer function for reference drive voltage.
D is the transfer function of the phase and gain mismatch between the measured real (in-phase) and measured imaginary (quadrature) components of the complex current and voltage. This mismatch is caused by imperfections in the circuit elements that do the measuring. D is also known as the "mixer transformation matrix". It is an object of the present invention to measure the value of D and to correct for its influence.

In the admittance measuring circuit 100, a generated source voltage 102 ($V_S$) is selectively applied to the cell or to one of a plurality of references through an associated transfer function as indicated by reference numerals 104, 106, and 108. When $V_s$ is applied to transfer function $A_C$ 104, a voltage $V_C$ is produced which is applied to the complex admittance for the cell, $Y_C$ 110. Similarly, when the voltage 102 ($V_S$) is applied to a first transfer function $A_R$ 106 the resulting voltage $V_{r1}$ is applied to the complex admittance of the first reference admittance, $Y_{R1}$ 112, and when the signal 102 is applied to the second transfer function $A_r$ 108, the resulting voltage $V_{R2}$ is applied to the second complex admittance 114 ($Y_{R2}$). Each of the resulting currents is summed in an adder 116. Where only one path is selected, only one of these signals will be nonzero. The resulting current is then $I_C$ if the cell is selected, $I_{R1}$ if the first reference is selected, and $I_{R2}$ if the second reference is selected. The resulting current flows through a circuit having transfer function H 120, H being a transfer function for converting complex current to a complex voltage for measurement purposes. The resulting voltage measured through node 121 represents the complex current through either the cell admittance or one of the reference admittances. The real and imaginary (in-phase and quadrature) components of this voltage are determined by applying the voltage to the subcircuit consisting of blocks 128, 129, and 130 as shown in FIG. 5. Thus in this manner, voltages $U_{Cm1}$ and $U_{Cm2}$ representing the complex current through the cell are measured. By selecting either of the references, voltages representing the complex current through the first reference or through the second reference can also be measured.

In addition to measuring voltages that represent the complex current values, voltages that represent the complex voltage values are also calculated according to the circuit. The voltages from the cell, $V_C$, the first reference, $V_{R1}$, and the second reference, $V_{R2}$ are applied to an adder 118. As only one of the references or the cell is selected at a time, only one of these values will be non-zero. The result is applied to a transfer function 126 resulting in a complex voltage at node 127. The real and imaginary (in-phase and quadrature) components of this voltage are determined by applying the voltage to the subcircuit consisting of blocks 128, 129, and 130 as shown in FIG. 5.

In this manner, the circuit shown in FIG. 5 provides for determination of the real and imaginary parts of both the voltage and the current associated with a particular admittance. This admittance being either that associated with the cell of the grain moisture sensor or that associated with one of the reference admittances of the grain moisture sensor.

To further explain, the following mathematical relationships are present:

$$G = \frac{W}{V}$$

$$H = \frac{U}{I}$$

In each case, the respective transfer functions are defined as the ratio of the output of the function to the input of the function.

In addition, the admittance is defined mathematically as:

$$Y = \frac{I}{V} = \frac{\frac{U}{H}}{\frac{W}{G}} = \frac{U}{W} \cdot \frac{G}{H}$$

Given these general relationships, the admittance of a reference is defined as:

$$YR = \frac{U_R}{W_R} \cdot \frac{G}{H}$$

Further, the empty cell admittance, YCE, and a full cell admittance, YCF, are calculated as follows:

$$Y_{CE} = \frac{U_{CE}}{W_{CE}} \cdot \frac{G}{H}$$

$$Y_{CF} = \frac{U_{CF}}{W_{CF}} \cdot \frac{G}{H}$$

If the measurements for the reference admittance and the cell admittance are done in the same environmental conditions, it can be assumed that both G and H are the same in the cell admittance equations and the reference admittance equations. Then the following characterizes the empty cell and reference calibration factor F:

$$\frac{W_R}{U_R} \cdot Y_R = \frac{W_{CE}}{U_{CE}} \cdot Y_{CE} \Rightarrow F = \frac{W_{CE}}{U_{CE}} \cdot \frac{U_R}{W_R} = \frac{Y_R}{Y_{CE}}$$

The reference calibration factor, F, gives the ratio of the reference admittance to the empty cell admittance at the same environmental conditions. Thus a reference admittance can be used instead of an empty cell admittance for calibration purposes.

Assuming that F will stay constant, the sampled grain's complex permittivity can be calculated as:

$$\varepsilon = \frac{U_{CF} \cdot W_R}{W_{CF} \cdot U_R} \cdot F$$

Where:

$$\epsilon = \epsilon' - j\epsilon''$$

Thus, the present invention provides for measurement of the complex permittivity of grain for moisture sensing purposes.

To make accurate current and voltage measurements it is necessary that the in-phase (IP) and quadrature (Q) local oscillator signals used with mixers 216, 220, and 224 to extract the real and imaginary components of complex signals have a phase difference of exactly 90 degrees and have identical amplitudes at their fundamental frequencies. Errors will be introduced to the extent that this is not the case. By using two reference admittances of known and stable values however, corrections to these errors are made.

The D functions 124 and 130 represent the distortion of the imaginary part with the respect to the real part of all measured complex values. All measured values $U_m$ and $W_m$ can be corrected, using the same formula to obtain U and W, which are the values before any measurement distortion error is introduced.

The following is the distorted relationship between the complex voltages representing cell and reference currents and their measured values:

$$U = [1\ jj] \cdot D^{-1} \cdot U_m$$

where:

$$D^{-1} = PFC = \begin{bmatrix} 1 & 0 \\ pfc1 & pfc2 \end{bmatrix}$$

$$U_m = \begin{bmatrix} U_{m1} \\ U_{m2} \end{bmatrix}$$

The same distorted relationship holds between the complex voltages representing cell and reference voltages and their measured values:

$$W = [1\ jj] \cdot D^{-1} \cdot W_m$$

where:

$$D^{-1} = PFC = \begin{bmatrix} 1 & 0 \\ pfc1 & pfc2 \end{bmatrix}$$

$$W_m = \begin{bmatrix} W_{m2} \\ W_{m2} \end{bmatrix}$$

Expanding the above equations gives $$U = U_{m1} + j \cdot (pfc1 \cdot U_{m1} + pfc2 \cdot U_{m2})$$

$$W = W_{m1} + j \cdot (pfc1 \cdot W_{m1} + pfc2 \cdot W_{m2})$$

The pfc1 and pfc2 correction factors are found through the use of two different references having known and stable admittance values of different phase angles. As an example, in one embodiment of the present invention the first reference is a temperature stable 1% capacitor (COG) with a value of 15 pF (admittance $Y_{R1}$) and the second reference is a precision 0.1% resistor with value of 2000 Ω (admittance $Y_{R2}$). Other reference values may be used as well.

The ratio of the reference admittances is computed as follows, with the example values also shown:

$$R = \frac{Y_{R1}}{Y_{R2}} = Q_R + j \cdot Q_1 = 2000 \cdot j \cdot (2\pi \cdot f \cdot 15 \cdot 10^{-12})$$

The ratio of the raw measurements of two references is:

$$Rm = \frac{U_{R1} \cdot W_{R2}}{W_{R1} \cdot U_{R2}}$$

Expanding the above equation to include the measured values results in:

$$Rm = \frac{(U_{R1m1} + j(U_{R1m1} \cdot pfc1 + U_{R1m2} \cdot pfc2)) \cdot (W_{R2m1} + j(W_{R2m1} \cdot pfc1 + W_{R2m2} \cdot pfc2))}{(W_{R1m1} + j(W_{R1m1} \cdot pfc1 + W_{R1m2} \cdot pfc2)) \cdot (U_{R2m1} + j(U_{R2m1} \cdot pfc1 + U_{R2m2} \cdot pfc2))}$$

$R_m$ is set equal to R and two quadratic equations in two unknowns (pfc1, pfc2) are derived:

$a_1 \cdot pfc_1^2 + b_1 \cdot pfc_2^2 + c_1 \cdot pfc_1 \cdot pfc_2 + d_1 \cdot pfc_1 + e_1 \cdot pfc_2 + f_1 = 0$
(from real part)

$a_2 \cdot pfc_1^2 + b_2 \cdot pfC_2^2 + c_2 \cdot pfc_1 \cdot pfc_2 + d_2 \cdot pfc_1 + e_2 \cdot pfc_2 + f_2 = 0$
(from imaginary part)

where:

$a_1 = Q_R \cdot W_{R1m1} \cdot U_{R2m1} - U_{R1m1} \cdot W_{R2m1}$ $a_2 = Q_I \cdot W_{R1m1} \cdot U_{R2m1}$ $b_1 = Q_R \cdot W_{R1m2} \cdot U^{R2m2} - U_{R1m2} \cdot WR2m2$ $b_2 = Q_I W_{R1m2} \cdot UR2m2$ $c_1 = Q_R \cdot W_{R1m1} \cdot U_{R2m2} + Q_R \cdot W_{R1m2} \cdot U_{R2m1} - U_{R1m1} \cdot W_{R2m2} - U_{R1m2} \cdot W_{R2m1}$ $c_2 = e_1$ $d_1 = 2 \cdot Q_I \cdot W_{R1m1} \cdot U_{R2m1}$ $d_2 = -2 \cdot a_1$ $e_1 = Q_I \cdot (W_{R1m1} \cdot U_{R2m2} + W_{R1m2} \cdot U_{R2m1})$ $e_2 = -c_1$ $f_1 = -a_1$ $f_2 = -a_2$ These two quadratic equations are then solved simultaneously for pfc1 and pfc2. As a simple closed form solution is not available, they may be solved by Newton-Raphson iteration for example. Other numerical equation solving algorithms may be used as well. The solution is known to be near the point (pfc1=0, pfc2=1) hence this is preferably used for a starting point. In theory four different solutions are possible. Any solution not near (0,1) shall be considered extraneous. In a software implementation, an appropriate error condition can be set. This is not likely to happen, however, if it does occur, precautions can be taken when the error condition is present.

Figure 6A:
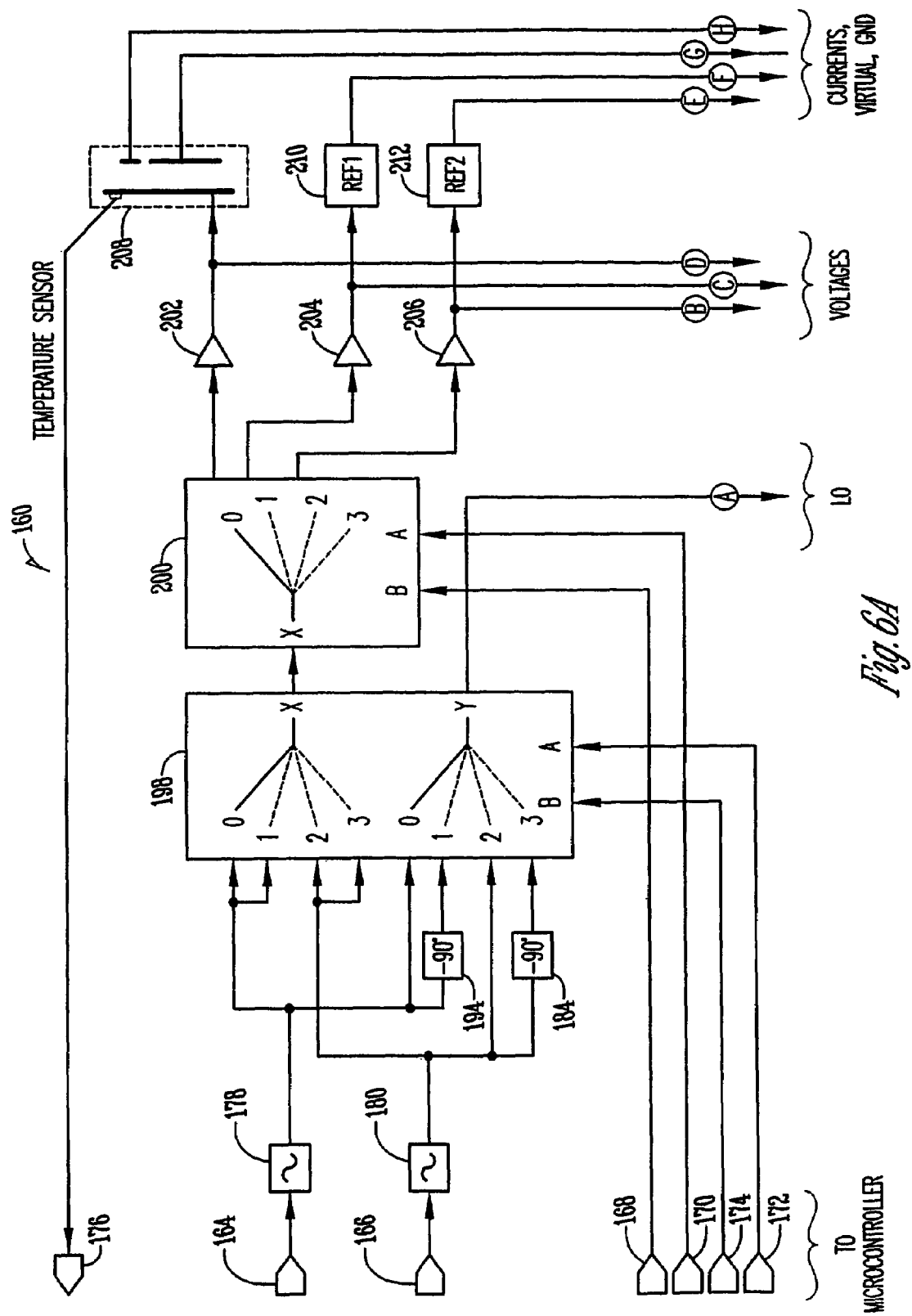
FIGS. 6A and 6B are block diagrams of the moisture sensor circuit according to the present invention.
Figure 6B:
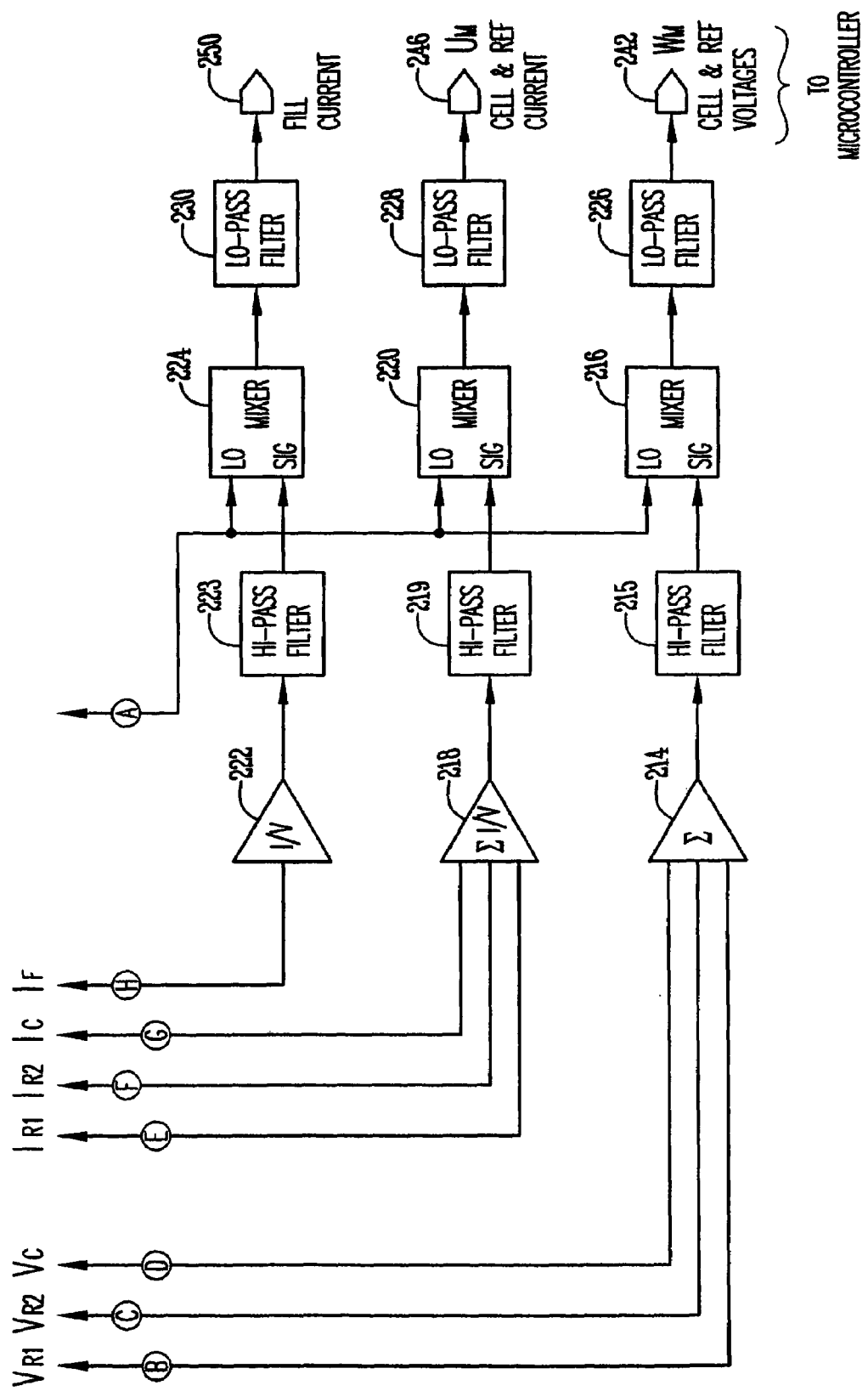

FIGS. 6A and 6B show a schematic of the grain moisture sensor according to the present invention. The schematic shows a number of input and output lines for connection to an intelligent control such as a processor, microcontroller, integrated circuit, or other device. This schematic shows merely one circuit configuration of the present invention. The present invention provides for the ability to selectively measure one of a plurality of complex admittances at a plurality of frequencies.

The inputs to the system (outputs from an intelligent controller) are shown in FIG. 6A. The inputs include a first frequency input 164 and a second frequency input 166. Optionally a first sine wave generator 178 and a second sine wave generator 180 are used. The sine wave generators take the square wave output of a microcontroller, divide the frequency as necessary, and smooth the output such that a sinusoidal signal is produced. The output from the first sine wave generator 178 is electrically connected to three switch inputs of dual quad switch 198. In addition, the output from the first sine wave generator 178 is electrically connected to a 90 degree phase shifter 194. The 90 degree phase shifter 194 is constructed such that its output signal is 90 degrees out of phase with its input signal. The 90 degree phase shifter 194 is electrically connected a switch input of the dual quad input switch 198. The output of the second sine wave generator 180 is similarly connected.

The first sine wave generator 178 and the second sine wave generator 180 operate at different frequencies. For example, the first sine wave generator 178 operates at 10 MHz while the second sine wave generator 180 operates at 1 MHz.

The dual quad input switch 198 is controlled by input 174 and input 172 that are used to select one of the signals. One of the outputs from the switch is electrically connected to an input of the dual quad output switch 200. Inputs 168 and 170 are connected to the switch 200 to control which of the outputs is selected. The outputs are buffered and then electrically connected to the sensor cell 208, a first reference admittance 210, and a second reference admittance 212. The reference admittances are used for calibration purposes.

As shown in FIG. 6B, the buffered outputs, which drive the cell and the two references, are also electrically connected to a summing circuit 214. The output from the summing circuit 214 is electrically connected, through high pass filter 215, to a mixer 216. This mixer 216 also has a local oscillator input electrically connected to an output from the switch 198 (FIG. 6A). The output of mixer 216 passes through low pass filter 226 and is then electrically connected to an analog-to-digital converter and read by the microcontroller. The output of the mixer 216 has a DC voltage that is proportional to that component of the input voltage signal that is in-phase with the local oscillator.

The sense plate of the sensor cell 208 and the first reference 210 and the second reference 212 of FIG. 6A are electrically connected to a summing current to voltage converter 218 shown in FIG. 6B. The summing current to voltage converter has a low impedance, virtual ground type of input. The output of the summing current-to-voltage converter is electrically connected, through high pass filter 219, to a second mixer 220. The second mixer 220 also has a local oscillator input electrically connected to an output from switch 198 (FIG. 6A). The output of mixer 220 passes through low pass filter 228 and is then electrically connected to an A/D converter and read by the microcontroller. The output of the mixer 220 has a DC voltage that is proportional to that component of the input signal that is in-phase with the local oscillator.

In addition, the current, $I_F$ from the fill plate on the sensor cell 208 (shown in FIG. 6A) passes through the current to voltage converter 222. This current to voltage converter also has a low impedance, virtual ground type of input. The output of the current to voltage converter 222 is electrically connected, through high pass filter 223, to a third mixer 224. The third mixer 224 also has a local oscillater input that is electrically connected to an output from switch 198. The output of mixer 224 passes through low pass filter 230 and then is electrically connected to an analog to digital converter and read by the microcontroller. This configuration permits monitoring of the admittance of the fill plate relative to that of the sense plate. When this relationship is proportional to the relative sizes of the plates, then the sensor cell 208 is considered full of grain.

The synchronous detection method for measuring complex signals through the use of a local oscillator, a mixer, and a low pass filter, as described above, has a very narrow band pass filtering effect, greatly reducing noise influence on the measurement. The virtual ground method of measuring very low-level currents is used to provide the advantage of a substantial reduction in the influence of parasitic elements at the current summing and sensing node.

Returning to FIG. 6A, a thermistor or other temperature sensor is attached to the driven plate of the sensor cell 208. This is only one example of temperature sensor placement. The temperature sensor may also be attached to one of the other plates in the cell. The measurement of temperature allows moisture calculations to be corrected accordingly.

Thus a detailed schematic for the present invention has been shown and described. That which is shown is merely one embodiment of a design according to the present invention. The present invention contemplates variations in the frequencies used, the number of references, the particular electrical components used to perform a particular function or set of functions, and other variations.

Therefore a novel grain moisture sensor has been disclosed. According to one aspect of the invention, the grain moisture sensor provides for the measurement of complex admittance at multiple frequencies. According to another aspect of the invention, the grain moisture sensor is mounted in the grain tank of a combine. According to another aspect of the present invention, the grain moisture sensor is of a sensor cell design that guards the capacitive plates from fringe effects. According to another aspect of the invention, a fill sensor is provided so that accurate determinations can be made as to when the sensor cell is full and ready for measurement.

ASSIGNMENT

The entire right, title and interest in and to this application and all subject matter disclosed and/or claimed therein, including any and all divisions, continuations, reissues, etc., thereof are, effective as of the date of execution of this application, assigned, transferred, sold and set over by the applicant(s) named herein to Deere & Company, a Delaware corporation having offices at Moline, Ill. 61265, U.S.A., together with all rights to file, and to claim priorities in connection with, corresponding patent applications in any and all foreign countries in the anem of Deere & Company or otherwise.

What is claimed is:

1. A grain moisture sensing system comprising:
    an excitation signal source for producing an excitation signal;
    a sensor cell having a driven plate for applying the excitation signal and a sense plate proximate to and substantially parallel with the driven plate for capacitive measurement across a spacing between the driven plate and the sense plate such that a sense current is produced at the sense plate;
    the excitation signal source electrically connected to the driven plate of the sensor cell;
    a first synchronous detector adapted for measuring components of the excitation signal, the synchronous detector electrically connected to the excitation source; and
    a second synchronous detector adapted for measuring components of the sense current, the second synchronous detector operatively connected to the sense plate.

2. The grain moisture system of claim 1 wherein the first synchronous detector is adapted for alternatively measuring imaginary components of the excitation signal and real components of the excitation signal.

3. The grain moisture system of claim 1 wherein the second synchronous detector is adapted for alternatively measuring imaginary components of the sense current and real components of the sense current.

4. The grain moisture system of claim 1 wherein the first synchronous detector is a mixer and the second synchronous detector is a mixer.

5. The grain moisture sensor of claim 1 wherein the excitation signal source is a switch adapted for alternatively selecting one of a first frequency in-phase signal, a first frequency quadrature signal, a second frequency in-phase signal, and a second frequency quadrature signal.

\* \* \* \* \*